(12) United States Patent
Jans et al.

(10) Patent No.: US 9,373,519 B2
(45) Date of Patent: Jun. 21, 2016

(54) METHOD TO PATTERN SUBSTRATES

(71) Applicant: IMEC VZW, Leuven (BE)

(72) Inventors: Karolien Jans, Leuven (BE); Alexandra Dusa, Leuven (BE); Tim Stakenborg, Leuven (BE)

(73) Assignee: IMEC VZW, Leuven (BE)

(*) Notice: Subject to any disclaimer, the term of this patent is extended or adjusted under 35 U.S.C. 154(b) by 0 days.

(21) Appl. No.: 14/560,202

(22) Filed: Dec. 4, 2014

(65) Prior Publication Data

US 2015/0155179 A1 Jun. 4, 2015

(30) Foreign Application Priority Data

Dec. 4, 2013 (EP) .................................... 13195678

(51) Int. Cl.
| | |
|---|---|
| H01L 21/306 | (2006.01) |
| H01L 21/308 | (2006.01) |
| H01L 29/06 | (2006.01) |
| H01L 21/3205 | (2006.01) |
| H01L 21/32 | (2006.01) |
| G01N 33/487 | (2006.01) |
| B82Y 40/00 | (2011.01) |

(52) U.S. Cl.
CPC ............ *H01L 21/3085* (2013.01); *B82Y 40/00* (2013.01); *G01N 33/487* (2013.01); *H01L 21/3086* (2013.01); *H01L 21/32* (2013.01); *H01L 21/32051* (2013.01); *H01L 29/06* (2013.01)

(58) Field of Classification Search
CPC . H01L 21/3085; H01L 21/3086; H01L 21/32; H01L 21/32051; H01L 29/06; B01L 3/5027; G01N 33/487
See application file for complete search history.

(56) References Cited

U.S. PATENT DOCUMENTS

| | | | | |
|---|---|---|---|---|
| 2003/0040173 | A1* | 2/2003 | Fonash | B01J 19/0093 438/622 |
| 2004/0075159 | A1* | 4/2004 | Vogeli | B01J 19/0093 257/618 |
| 2005/0255514 | A1 | 11/2005 | De Palma et al. | |
| 2008/0286767 | A1* | 11/2008 | Miyahara | B01L 7/00 435/29 |
| 2013/0043551 | A1* | 2/2013 | Yoshizawa | H01L 29/06 257/432 |
| 2013/0115382 | A1* | 5/2013 | Chiari | B01L 3/5027 427/535 |
| 2015/0147886 | A1* | 5/2015 | Tung | C23G 1/02 438/696 |

FOREIGN PATENT DOCUMENTS

EP  1 607 743 A1  12/2005

OTHER PUBLICATIONS

Jackson, Bryan L. et al., "Hybrid Protein—Lipid Patterns from Aluminium Templates", Langmuir, vol. 23, 2007, pp. 2052-2057, Published on Web Dec. 23, 2006.

* cited by examiner

*Primary Examiner* — Allan R Wilson
(74) *Attorney, Agent, or Firm* — McDonnell Boehnen Hulbert & Berghoff LLP

(57) ABSTRACT

A method for creating a pattern on a substrate (101) is presented, the method comprises: providing a substrate (101) comprising silicon; creating a sacrificial layer (102) on the substrate (101), wherein the sacrificial layer is formed on a first surface area (101*a*) of the substrate thereby leaving a second surface area (101*b*) exposed; depositing a first functional layer (103) at least on the second surface area (101*b*) of the substrate (101); removing the sacrificial layer (102); wherein: removing the sacrificial layer (102) is performed by etching the sacrificial layer (102) with an acidic aqueous solution that does not adversely affect the first functional layer (103) and the substrate (101).

13 Claims, 11 Drawing Sheets

METHOD TO PATTERN SUBSTRATES

FIELD OF THE DISCLOSURE

The disclosure relates to techniques for creating patterns on substrates. Further, the disclosure relates to micro-fluidic devices and techniques to pattern such devices.

BACKGROUND TO THE DISCLOSURE

Techniques to create patterns on silicon substrates using a sacrificial layer are known. A state of the art technique to create a pattern on a substrate is described in Jackson, B. L.; Groves, J.; "Hybrid Protein-lipid patterns form aluminum templates", Langmuir 2007, 23 (4) 2052-2057. An aqueous aluminum lift-off process suitable for the fabrication of hybrid patterns of protein and supported lipid membrane on surfaces is described. An aluminum layer is used as a sacrificial layer to create a pattern on a surface. The document states that the major drawback of the technique is the necessary pH for effective aluminum removal. The three-dimensional structures of many proteins are extremely sensitive to pH. Hence, these structures are damaged by etching products with a high pH value. As a solution, the document proposes to use methods that delay protein binding until after aluminum dissolution. These could include reactive monolayers that both resist vesicle adsorption and retain reactivity after prolonged incubation in basic or acidic conditions. As an alternative solution, a highly stable linking protein such as streptavidin could be employed.

SUMMARY OF THE DISCLOSURE

We recognized a need for a process to create patterns with lithographic accuracy on the surface of a substrate whereby one or more functional layers present on the surface can be maintained during the process.

In a first aspect of the disclosure, a method for creating a pattern on a substrate is presented. The method comprises providing a substrate; creating a sacrificial layer on the substrate, wherein the sacrificial layer is formed on a first surface area of the substrate thereby leaving a second surface area exposed; depositing a first functional layer at least on the second surface area of the substrate; removing the sacrificial layer; wherein the sacrificial layer removal is performed by etching the sacrificial layer with an acidic aqueous solution that does not adversely affect the first functional layer or the substrate.

According to an embodiment of the disclosure, the acidic aqueous solution has a pH value between 0 and 8.

According to an embodiment of the disclosure, removing the sacrificial layer is performed by etching the sacrificial layer with an acidic solution having a pH value between 0 and 8.

According to an embodiment the sacrificial layer comprises a metal or a metal oxide. According to an embodiment of the disclosure, the sacrificial layer comprises Aluminum Oxide or Germanium Oxide.

According to an embodiment of the disclosure, the method further comprises depositing a second functional layer on the substrate and wherein the second functional layer only binds to the first surface area of the substrate.

According to an embodiment of the disclosure, the substrate comprises a biosensing region underlying and in contact with the sacrificial layer.

According to an embodiment of the disclosure, the acidic aqueous solution comprises phosphoric acid, nitric acid, sulfuric acid, hydrochloric acid or acetic acid or a combination thereof.

According to an embodiment of the disclosure, the substrate forms a wall of a micro-fluidic channel and removing the sacrificial layer is performed by propagating an etching product through the micro-fluidic channel.

According to an embodiment of the disclosure, the micro-fluidic channel is a closed micro-fluidic channel.

According to an embodiment of the disclosure, the first functional layer is an antifouling coating and the second functional layer is a functional coating or vice versa.

According to an embodiment of the disclosure, the first functional layer and/or the second functional layer consist of silane. According to an embodiment of the disclosure the second functional layer is an N3-SAM. According to an embodiment of the disclosure the first functional layer is a PEO-silane layer.

In a second aspect of the disclosure, an intermediate device suitable for integration with a biosensor is presented comprising a substrate comprising silicon and a sacrificial layer overlying at least a first surface area of the substrate, wherein the sacrificial layer is fabricated from a material that is removable by an acidic aqueous solution having a pH value between 0 and 8.

According to an embodiment of the disclosure, the intermediate device further comprises a first functional layer overlying the substrate and the sacrificial layer.

According to an embodiment of the disclosure, the intermediate device further comprises a biosensing region underlying and in contact with the sacrificial layer.

According to an embodiment of the disclosure, the substrate forms a wall of a micro-fluidic channel and the sacrificial layer is accessible to a fluid propagating through the micro-fluidic channel.

According to an embodiment of the disclosure, the micro-fluidic channel is a closed micro-fluidic channel.

BRIEF DESCRIPTION OF THE DRAWINGS

FIG. 1 A-D illustrate different steps to create a pattern on a substrate using one functional layer.

FIG. 2 A-E illustrate different steps to create a pattern on a substrate using two functional layers.

FIG. 3 A-D illustrate different steps to create a pattern on a substrate comprising a biosensor using one functional layer.

DESCRIPTION OF THE DISCLOSURE

Throughout the description reference is made to "anti-fouling" coating. This refers to a bio-fouling coating that may be used to prevent or slow down bio-interactions with, e.g., a surface. Such a coating may be present on a substrate to prevent or slow down bio-interactions with the substrate.

Throughout the description reference is made to a "substrate". In embodiments, the term "substrate" may include a substrate such as, for example, a silicon (Si) substrate, a silica (SiO2) substrate, a silicon nitride (SiN) substrate, a silicon germanium (SiGe) substrate or a glass silica substrate. It may also refer to the ensemble of one or more layers present on that substrate, e.g., an isolating layer on a silicon substrate wherein the substrate comprises an isolating layer and a silicon substrate. The term "substrate" also includes silicon-on-glass, silicon-on-sapphire substrates. Accordingly, a substrate may be a wafer such as a blanket wafer or may be a layer applied to another base material.

Throughout the description reference is made to "a functional layer". This refers to a layer that may bind a bioreceptor for binding a biomolecule of interest to a surface. This may also refer to a layer with any other functionality such as, for example, a fouling functionality for preventing deposition or growth of a material on a surface, a hydrophobic functionality, or a hydrophilic functionality.

The disclosure discloses a technique to create a pattern on a substrate. The use of one or more sacrificial layers for creating a pattern on a substrate is described. The sacrificial layer is first deposited in a certain pattern on a silicon substrate. The material of the sacrificial layer is a material that can be removed using an acidic aqueous solution. A functional layer is deposited on top of the substrate and the sacrificial layer. Thereafter, the sacrificial layer is removed. The material for the sacrificial layer is selected based on its dissolving properties when immersed in an acidic aqueous solution. The use of an acidic aqueous solution allows preservation of other functional layers that are present on the silicon substrate. By removing the sacrificial layer, any material that was deposited on the sacrificial layer such as the functional layer is also removed. Optionally, another functional layer is deposited on the substrate to create another functional layer on the surface of the silicon substrate. The substrate now comprises a pattern of two different functional layers.

In a first aspect of the disclosure, a method to create a pattern on a substrate is presented. The method comprises: providing a substrate 101 comprising silicon; creating a sacrificial layer 102 on the substrate 101 wherein the sacrificial layer is formed on a first surface area 101a of a surface of the substrate 101 thereby leaving a second surface area 101b exposed; depositing a first functional layer 103 at least on the second surface area 101b of the substrate 101; removing the sacrificial layer 102; wherein removing the sacrificial layer is performed by etching the sacrificial layer with an acidic aqueous solution or acidic solution that does not adversely affect the first functional layer 103 or the substrate 101.

The first functional layer has functional properties or anti-adhesive properties which are not adversely affected by the acidic aqueous solution. Hence, the acidic aqueous solution is selected such that it does not affect the first functional layer. By doing so, the first functional layer can still prevent binding of a certain type of biomolecule or repel biomolecules after removal of the sacrificial layer. Because the first functional layer (e.g. a SAM) is not compatible with high pH, the material of the sacrificial layer is selected such that it may be removed at low/neutral pH.

According to an embodiment of the disclosure, the substrate 101 is a silica, a silicon or a glass substrate. According to an embodiment of the disclosure, at least one layer (e.g., an isolating layer) may be present between the substrate and the sacrificial layer 102. Also metallic substrates are included. Such metallic substrates may be electrodes for electrochemical detection such as TiN electrodes. After oxidation, you form on TiN also a thin layer of TiO2 on which SAM's with silanes can be formed.

FIG. 1A-D illustrate the different steps of the method.

Figure 1A:
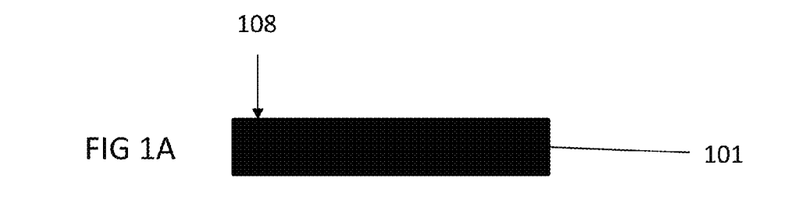

FIG. 1A illustrates a substrate 101. The substrate may be patterned using CMOS compatible processing steps allowing manufacturing in mass production thereby reducing the total cost of each patterned substrate 101.

Figure 1B:
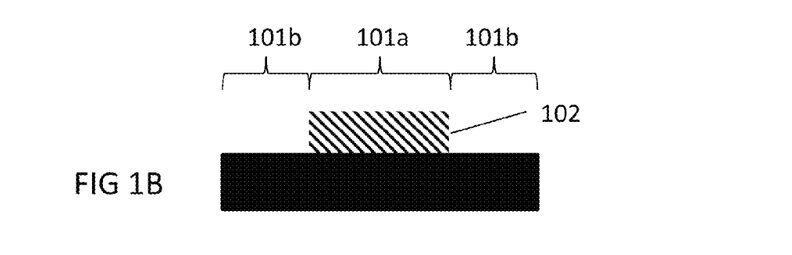

FIG. 1B illustrates creating a sacrificial layer 102 on the substrate 101. The sacrificial layer is created on a surface of the substrate 101, e.g., on a top surface 108 of the substrate 101. According to an embodiment of the disclosure, the substrate 101 may comprise another layer, e.g., an isolating or an adhesion layer, on which the sacrificial layer 102 is created. A first surface area 101a of the top surface 108 of the substrate 101 or a first surface area 101a of a layer on top of the substrate 101 may be covered with the sacrificial layer 102. A CMOS compatible process may be used to create the sacrificial layer 102. According to an embodiment of the disclosure, the sacrificial layer 102 is created using standard lithographic techniques. For example, the use of atomic layer deposition (ALD) allows the sacrificial layer 102 to be deposited on the substrate 101 in a thin and uniform way. As an advantage, a thin sacrificial layer (film) can be easily etched. According to an embodiment of the disclosure, the sacrificial layer 102 is further patterned using an etch step, e.g., a wet etch step. The sacrificial layer 102 is fabricated from a material that can be etched using an acidic aqueous solution. Advantageously, the sacrificial layer can be removed from the substrate 101 or from another layer without damaging the substrate 101, other fragile layers present on the substrate 101, e.g., a layer or an electrical component underneath the sacrificial layer or other functional layers present on the substrate 101.

Figures 1C, 1D:
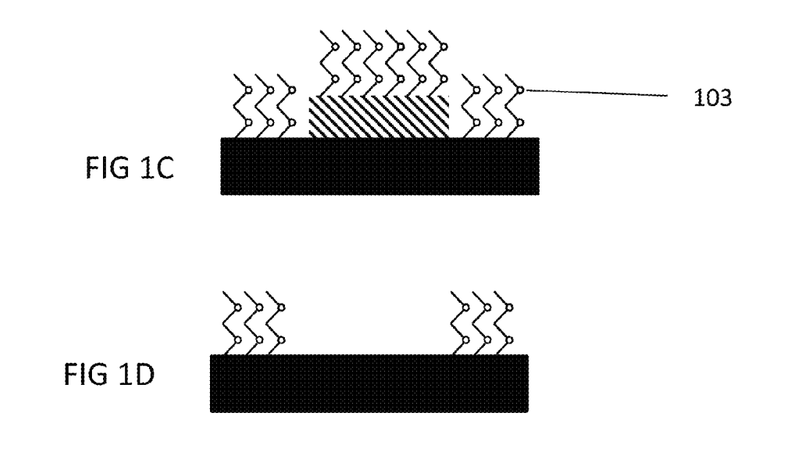

FIG. 1C illustrates the deposition of a first functional layer 103 on the substrate 101. The first functional layer 103 may be deposited at least on a second surface 101b of the substrate 101. The first functional layer 103 may be completely deposited on a top surface 108 of the substrate 101. The first functional layer 103 binds to the second surface area 101b of the surface of the substrate 101 and to the surface of the sacrificial layer 102. According to an embodiment of the disclosure, the first functional layer 103 is a layer that covalently binds to the substrate surface. According to an embodiment of the disclosure, the first functional layer 103 is an anti-fouling coating, e.g., PEO-silane. According to an embodiment of the disclosure, the first functional layer 103 is a self-assembled monolayer. Alternatively the first functional layer 103 is a multilayer. According to an embodiment of the disclosure, an Si—O—Si bond is formed between the first functional layer 103 and the substrate 101. In a particular embodiment of the disclosure, the first functional layer 103 comprises silane or is a silane layer, e.g., a polyethylene oxide modified silane layer (PEO). According to an embodiment of the disclosure, the first functional layer 103 is a hydrophobic or a hydrophilic layer. For example, the first functional layer 103 may be a Teflon layer.

FIG. 1D illustrates the removal of the sacrificial layer 102. According to an embodiment of the disclosure, the sacrificial layer 102 is removed using a wet etch process step. The product used to remove sacrificial layer 102 is an acidic aqueous solution. In a particular embodiment of the disclosure, the etching product is an aqueous phosphoric acidic solution. The etching product may be a product that etches neither the material of the substrate 101 nor the first functional layer 103. As an advantage, the sacrificial layer may be removed from the substrate 101 without damaging the substrate or the surface of the substrate itself, the first functional layer 103 and/or other fragile layers or components present on the substrate 101, e.g., a layer or an electrical component underneath the sacrificial layer.

Figure 1E:
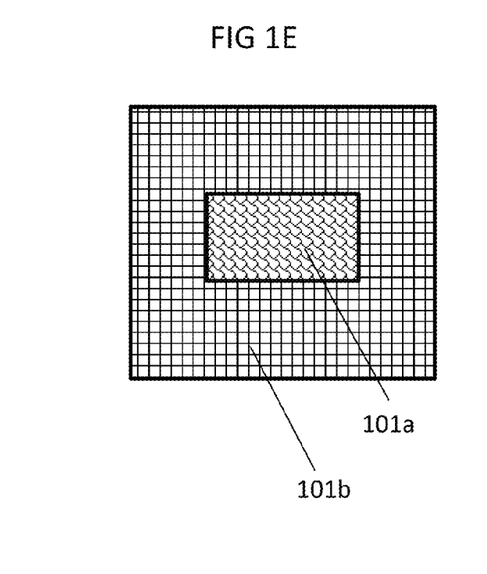
FIG. 1E illustrates a top view of a substrate comprising a pattern.

FIG. 1E illustrates a top view of an embodiment of a surface of a substrate 101. Indicated are a first surface area 101a and a second surface area 101b.

According to an embodiment of the disclosure, the first functional layer consists of silane. According to an embodiment of the disclosure, the first functional layer 103 is a silane layer. Si—O—Si bonds formed between the substrate 101 and the silane layer must be maintained when removing the sacrificial layer to preserve the integrity and the adherence of the silane layer to the substrate 101. Further, if the silane layer comprises polyethylene oxide (PEO) units it is important not to remove these units as this may reduce anti-fouling properties of the silane layer. The material of the sacrificial layer 102 is selected to allow removal of the sacrificial layer 102 using aqueous acidic etching products without breaking the Si—O—Si bonds or removing PEO units of the first functional layer.

Figure 11:
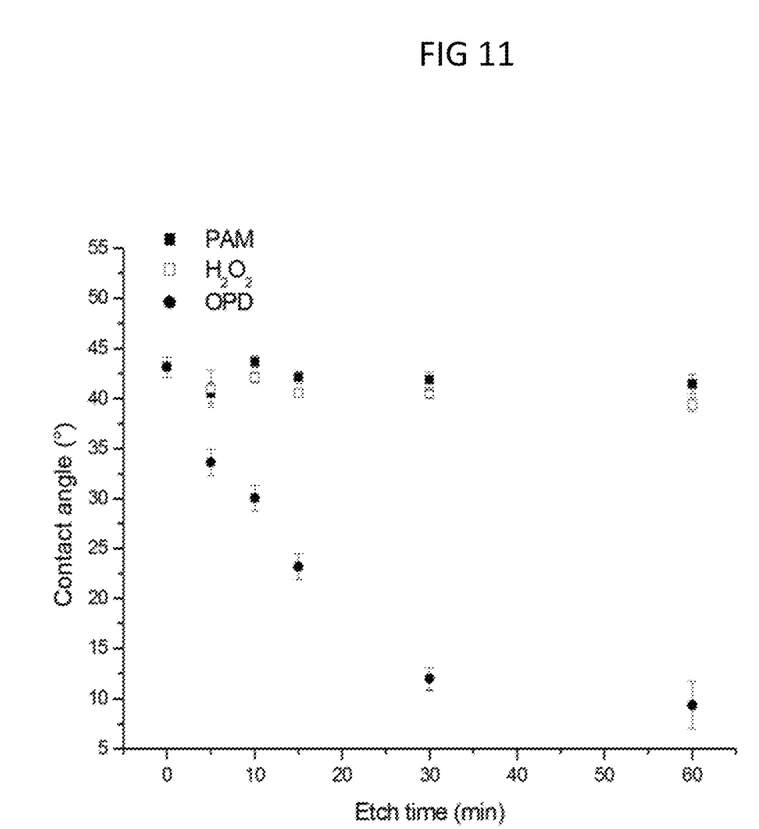
FIG. 11 illustrates contact angle measurements on a PEO6/9-SAM functionalized $SiO_2$ sample after etching for different times in PAM, $H_2O_2$ and OPD.

As illustrated in FIG. 11, during experiments it was observed that the integrity of a functional layer (PEO6/9 SAM) cannot be maintained after etching in a basic acidity solution (basic OPD—tetra methyl ammonium hydroxide) solution. However, when using aqueous acidic etching products such as PAM (a phosphoric acid mixture), the functional layer (PEO6/9 SAM) can be maintained.

Further, it is an advantage that only the sacrificial layer 102 and, as a result, the first functional layer 103 bound to the sacrificial layer 102 are removed. Hence, the first surface area 101a of the surface of the substrate 101 that was covered by the sacrificial layer 102 is cleared and can bind another functional layer. If the sacrificial layer 102 is deposited on a surface area of a biosensor present on the substrate 101, the surface area of that biosensor is cleared after removal of the sacrificial layer 102 and can then be used to bind another functional layer or adsorb biomolecules. As can be noticed in FIG. 1D; a pattern is created wherein a second surface area 101b of the surface of the substrate 101 is covered with the first functional layer 103 and wherein a first surface area 101a of the surface of the substrate 101 is material-free.

According to an embodiment, the method may also be defined as a method for selectively functionalizing a biosensing circuitry wherein the substrate comprises a biosensor and wherein within the first surface area of the substrate the biosensor is present. Thus, a sacrificial layer covering the first surface area also covers the biosensor.

According to an embodiment of the disclosure, the aqueous acidic solution is a solution with a pH between 0 and 8. According to an embodiment of the disclosure, the maximum pH value of the aqueous acidic solution is 8. According to an embodiment of the disclosure, the acidic aqueous solution comprises phosphoric acid. Alternatively, the sacrificial material can be removed by other low pH solutions, such as mixtures with HCl, $H_2SO_4$, HBr, HI, or organic acids such as acetic acid, while HF is excluded and cannot be used to lower the pH because it also etches the siloxane bond (Si—O—Si). Also, oxidizing agents and mixtures thereof (e.g., $H_2O_2$ and HCl/HNO_3 (aqua regia)) should be avoided because they attack the coating. For example, when AlOx is used as the sacrificial material, 1:10 HCl etches AlOx at a rate of 1.2 nm/min. According to an embodiment of the disclosure, etching can be further enhanced by adding a chelating compound that enhances the solubility of the sacrificial layer without affecting the first functional layer.

In a particular embodiment of the disclosure, the sacrificial layer comprises aluminum oxide (e.g., $Al_2O_3$), i.e., the sacrificial layer is an aluminum oxide layer. Compared to the material of sacrificial layers used in state of the art techniques, Aluminium oxide has multiple advantages: a) Aluminum oxide may be deposited as a thin and uniform layer on the substrate 101 (e.g., using ALD); b) Aluminum oxide is a material that can easily be processed in a CMOS processing line thereby reducing processing costs; and c) Aluminum oxide is a material that can be etched from the substrate 101 using aqueous acidic etching products. It is a further advantage of the disclosure that post-processing steps involving high temperatures may be performed on the substrate comprising the sacrificial layer because aluminum oxide or germanium oxide can resist these high temperatures. In other words, the sacrificial layer does not disintegrate. This is advantageous compared to, for example, using photoresist materials as a sacrificial layer because they are affected by such high temperatures. For example, when the substrate is a wall of a micro-fluidic channel, the micro-fluidic channel may be closed with a lid using anodic bonding techniques. The anodic bonding requires high temperatures that would affect the sacrificial layer if not resistant to these high temperatures.

According to an embodiment of the disclosure, the sacrificial layer may be a metal such as Al or Ni. These materials may be etched using a $H_3PO_4$-mix. In another embodiment, other oxides such as DyO or LaO might be used as they are also soluble in the proposed low pH etch solutions. In principle, any material that is soluble in a pH range between 0-8 can be used.

In general, the sacrificial layer can comprise any metal that can be etched using low pH etching chemicals. This is in contrast to prior art methods, such as discussed in the background section (above), which suggest using functional layers that are resistant to high pH etching chemicals. Using low pH is advantageous because biosensors positioned beneath the sacrificial layer will not be damaged by low pH. Preferably, the sacrificial layer material is temperature resistant to allow post processing, such as anodic bonding (high temperatures).

Figure 2A:
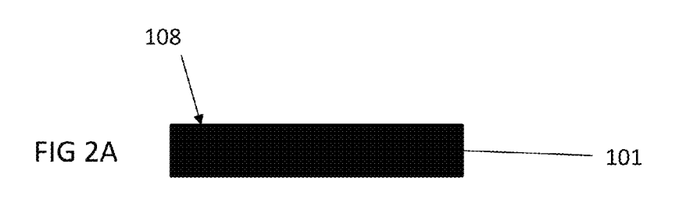
Figure 2B:
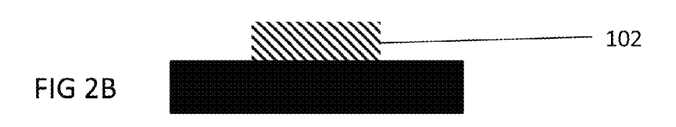
Figure 2C:
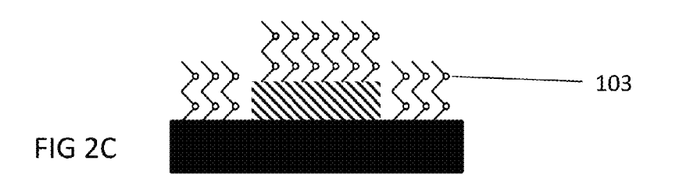
Figures 2D, 2E:
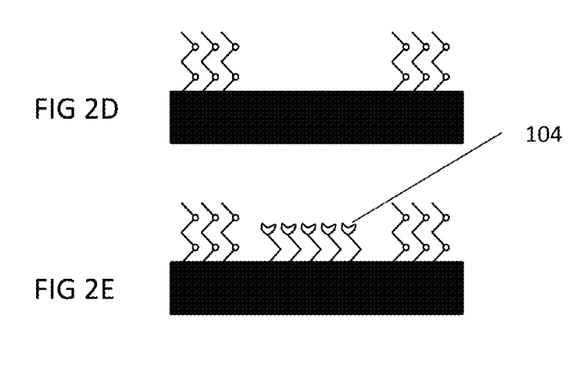

According to an embodiment of the disclosure, the method further comprises: depositing a second functional layer 104 on the substrate 101 wherein the second functional layer 104 only binds to a first surface area 101a of the substrate 101 that was previously covered by the sacrificial layer 102. The second functional layer 104 does not bind to the first functional layer 103. The second functional layer 104 may be a functional coating. The second functional layer 104 may be a self-assembled monolayer. The second functional layer 104 may be a multilayer. The second functional layer 104 may be a silane layer. The second functional layer may be a layer configured to bind biomolecules of interest, e.g., a 3-aminopropyl triethoxy silane layer (APTES). According to an embodiment of the disclosure, the second functional layer 104 consists of silane. According to an embodiment of the disclosure the second functional layer 104 is an $N_3$-SAM (Azide-silanization).). According to other embodiments, for the second functional layer other silanes may be used, e.g., silanes comprising an epoxy group or an NHS ester. Reference is made to EP1607743A1 and US20050255514A1, which disclose lists of active groups that may be used. The step illustrated in FIG. 2A-2E illustrate the different steps of the method wherein the steps depicted in FIG. 2A-FIG. 2D are identical to the steps depicted in FIG. 1A-1D. FIG. 2E illustrates the deposition of a second functional layer 104 on the substrate 101. The second functional layer 104 binds to the first surface area 101a of the substrate 101 that was previously covered by the sacrificial layer 102. According to an embodiment of the disclosure, the second function layer 104 is a hydrophobic or a hydrophilic layer.

According to an embodiment of the disclosure, the substrate 101 comprises a biosensing region 105 underlying and in contact with the sacrificial layer 102. The sacrificial layer 102 is created on top of the biosensing region 105. After removal of the sacrificial layer 102, a second functional layer 104 may be deposited on the biosensing region 105. The biosensing region 105 may be used to measure bio-signals of biomolecules bound to the biosensing region 105. Biomolecules of interest may bind to the biosensing region 105 if a functional layer is present on the biosensing region 105 and configured to bind biomolecules of interest. Alternatively, if a functional layer is not present on the biosensing region 105, biomolecules of interest may also be adsorbed on the surface of the biosensing region 105. The biosensing region 105 may be located on top of a top surface 108 of the substrate 101. The biosensing region 105 may be partly embedded in the substrate 101 wherein at least a top surface 109 of the biosensing region 105 is accessible to a fluid provided on the substrate 101 to allow biomolecules in the fluid to bind to the biosensing region 105. The biosensing region 105 may be a biosensing component such as a biosensing electronic circuit, a CMOS biosensing circuit, e.g., a CMOS bio-sensor.

The method to create a pattern on a substrate 101 as disclosed in the first aspect of the disclosure is particularly useful for biosensing applications as it allows site specific biomolecule deposition on a biosensing region 105 or any region of interest while other functional layers (e.g., present on the rest of the surface of the silicon substrate) are preserved. For example, anti-fouling properties of a functional layer present on the substrate 101 may be preserved when removing the sacrificial layer 102. When anti-fouling properties can be preserved, biomolecules only bind to the biosensing region 105 (or to a functional layer present on the biosensing region 105); this increases the sensitivity of the biosensing region 105. The method allows the sacrificial layer to be removed using acidic aqueous etching products, this reduces possible damage to sensitive electronic circuitry that may be part of the biosensing region 105 and leaves other functional layers on the substrate 101 intact.

Figure 3A:
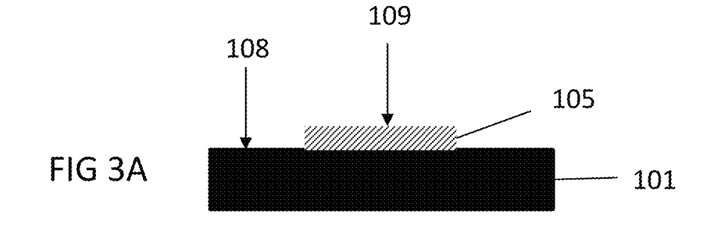
Figure 3B:
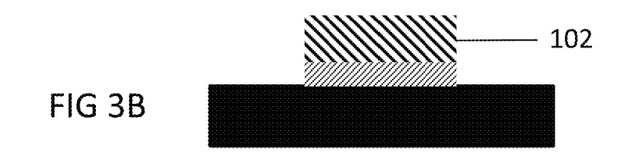
Figure 3C:
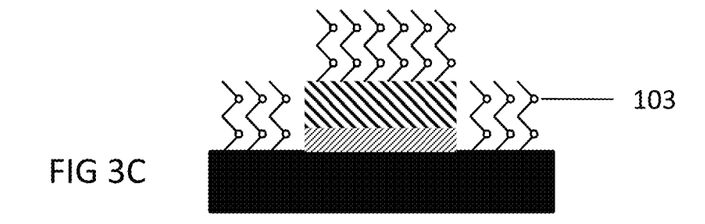
Figure 3D:
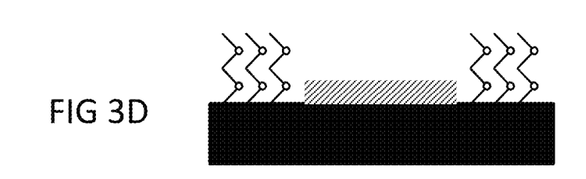

FIG. 3A-D illustrates an embodiment wherein a pattern is created on a substrate 101 comprising a biosensing region 105. FIG. 3A illustrates a device comprising a substrate 101 and a biosensing region 105. The biosensing region 105 is positioned on top of a top surface 108 of the substrate 101. FIG. 3B illustrates a sacrificial layer 102 that is created on top of a top surface 109 of the biosensing region 105. FIG. 3C illustrates a first functional layer 103 deposited on the substrate 101 and on the sacrificial layer 102. FIG. 3D illustrates the removal of the sacrificial layer 102 from the biosensing region 105.

Figure 4A:
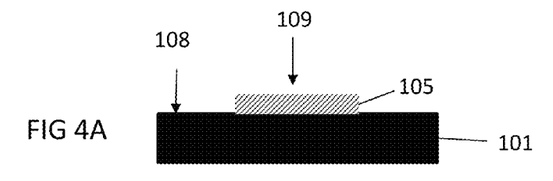
FIG. 4A-E illustrate different steps to create a pattern on a substrate comprising a biosensor using two functional layers.
Figure 4B:
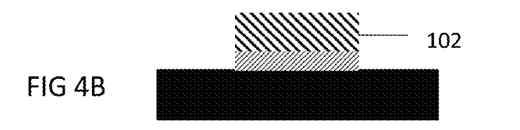
Figure 4C:
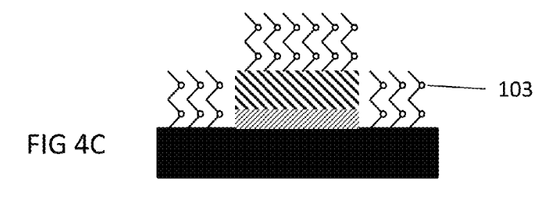
Figure 4D:
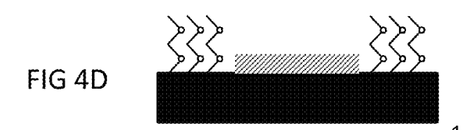
Figure 4E:
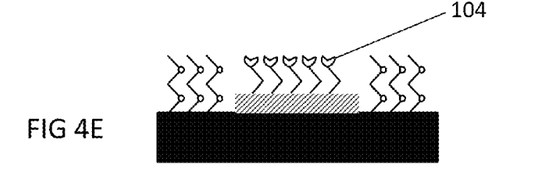

FIG. 4A-4E illustrate the different steps to create a pattern on a substrate 101 comprising a biosensing region 105 wherein the steps depicted in FIG. 4A-FIG. 4D are identical to the steps depicted in FIG. 3A-3D. FIG. 4E illustrates a second functional layer 104 being deposited on a top surface 109 of the biosensing region 105. The second functional layer 104 binds only to the top surface 109 of the biosensing region 105 and not to a first functional layer 103. The second functional layer 104 may be selected and configured to bind biomolecules of interest.

EXAMPLE

A substrate 101 with a biosensing region 105 is provided. The biosensing region 105 is covered with an Aluminum oxide layer (sacrificial layer 102). A first coating, a polyethylene oxide modified silane layer (first functional layer 103) known to reduce non-specific protein interactions, is deposited on the surface of the entire substrate 101 and on the Aluminum oxide layer. Thereafter, the Aluminum oxide layer that was deposited onto the biosensing region 105 is etched. Thereafter, the biosensing region 105 is modified with a functional coating, e.g., a functional silane layer with amino or azide end groups (second functional layer 104), to allow selective binding of biomolecules.

According to an embodiment of the disclosure, the substrate 101 forms a wall of a micro-fluidic channel 106 wherein the sacrificial layer 102 is accessible to a fluid propagating through the micro-fluidic channel 106. Removing the sacrificial layer 102 is performed by propagating or flowing an aqueous acidic etching product through the micro-fluidic channel 106. In a particular embodiment of the disclosure, the micro-fluidic channel 106 is a closed micro-fluidic channel. The method to create a pattern on a substrate as presented in the first aspect of the disclosure is particularly useful for creating patterns of different functional layers inside closed micro-fluidic channels.

In a first stage, a micro-fluidic channel 106 may be manufactured wherein a sacrificial layer 102 is created on a surface of an inner wall of the micro-fluidic channel 106. In a second stage, a first functional layer 103 may be deposited on inner surfaces of the micro-fluidic channel 106 by propagating a fluid or vapour comprising the first functional layer 103 through the micro-fluidic channel 106. In a third stage, the sacrificial layer 102 may be removed by flowing an aqueous acidic etching product through the micro-fluidic channel 106. In a fourth stage, a fluid or vapour comprising the second functional layer 104 may be propagated through the micro-fluidic channel 106. The vapour phase based deposition is less hampered by organic solvent waste, micelle formation, and diffusion limited transport. Even more importantly, vapour phase processes are better adapted to industrial requirements. The lower molecular density in the vapour phase helps to decrease the extent of self-polymerization of the organo-silane, resulting in more reproducible and smooth films. Especially for the coating of surfaces, such as walls vertical to the substrate of biosensor structures, e.g., ring resonators, much better reproducibility and uniformity can be achieved.

When the micro-fluidic channel 106 is a closed channel, it is not possible to use dry etching techniques using masks to remove the sacrificial layer 102. Thus, fragile functional layers and components present on inner walls of the micro-fluidic channel 106 cannot be protected when removing the sacrificial layer 102. When using an aqueous acidic etching product to remove the sacrificial layer, masks are not needed as functional layers that are present on inner walls of the micro-fluidic channel 106 are not damaged by the etching product. Further, the selection of the material of the sacrificial layer depends on the type of etching product. When an aqueous acidic etching product is used, the material may be Aluminum Oxide or another material that can be etched with that aqueous acidic etching product.

It is an advantage of the disclosure that site selective functionalization, such as an area on the substrate (e.g., a biosensor), can be achieved with lithographic accuracy.

Figure 5:
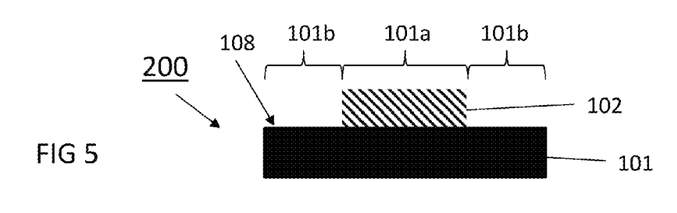
FIG. 5 illustrates an intermediate device with a sacrificial layer.

In a second aspect of the disclosure, an intermediate device suitable for integration with a biosensor is presented. The device comprises a substrate 101 comprising silicon and a sacrificial layer 102 overlying at least a first surface area 101a of the substrate 101, wherein the sacrificial layer 102 is fabricated from a material that is removable with an acidic aqueous solution having a pH between 0 and 8. The device presented in the second aspect of the disclosure is an intermediate device as it may be used in the process of manufacturing a final device. For example, the final device may be manufactured by using the intermediate device and etching the sacrificial layer. The area of the substrate 101 previously covered by the sacrificial layer 102 can then be functionalized by depositing another functional layer on that area. The sacrificial layer 102 covers a first surface area 101a of a top surface 108 of the substrate 101. The geometry of the sacrificial layer 102 depends on the pattern to be created on the substrate 101. The shape of the sacrificial layer 102 depends on the mask used to create the sacrificial layer 102 and may be any shape. Such an embodiment is illustrated in FIG. 5.

According to an embodiment of the disclosure, the sacrificial layer 102 comprises Aluminum oxide, e.g., the sacrificial layer is an Aluminum oxide layer. Aluminum oxide proves to be a material that may easily be removed with aqueous acidic etching products. Advantageously, the Aluminum oxide layer can be removed without damaging other parts of the device, e.g., the substrate 101. As a further advantage, a first functional layer 103 may be preserved when removing the sacrificial layer due to the acidity of the etching products used.

Figure 6:
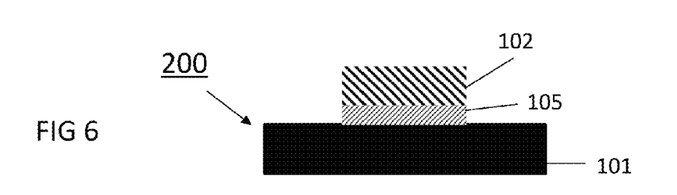
FIG. 6 illustrates an intermediate device with a sacrificial layer and a biosensing region.

According to an embodiment of the disclosure, the intermediate device comprises a biosensing region 105 underlying and in contact with the sacrificial layer 102. The sacrificial layer 102 may be located only on top of a surface of the biosensing region 105, e.g., the sensing surface. The biosensing region 105 may be a biosensor, e.g., an electronic biosensing circuit. The biosensor may be a CMOS biosensor. The biosensor may be a ring resonator structure. The biosensing region 105 may be partly or fully embedded in the substrate 101 wherein a sensing surface of the biosensing region 105 is accessible to a fluid provided on the substrate 101. According to an embodiment of the disclosure, the sacrificial layer 102 may cover a part or the entire surface of the biosensing region 105. The sacrificial layer 102 may be removed using aqueous acidic etching products. Advantageously, the biosensing region 105 is not damaged during removal of the sacrificial layer 102. Such an embodiment is illustrated in FIG. 6.

Figure 7:
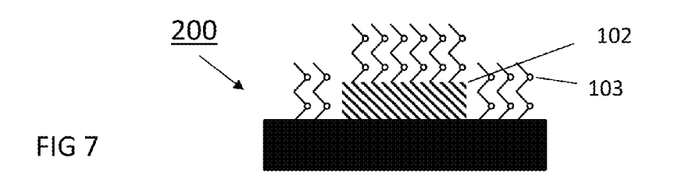
FIG. 7 illustrates an intermediate device with a sacrificial layer and a functional layer.
Figure 8:
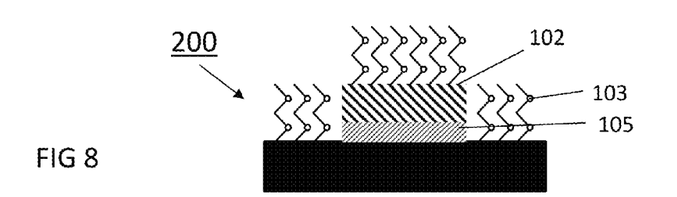
FIG. 8 illustrates an intermediate device with a sacrificial layer, a biosensing region and a functional layer.

According to an embodiment of the disclosure, the intermediate device further comprises a first functional layer 103 overlying the substrate 101 and the sacrificial layer 102. The first functional layer 103 covers the top surface 108 of the substrate 101 and the surface of the sacrificial layer 102 located on top of the substrate 101. Such an embodiment is illustrated in FIG. 7 and FIG. 8. In FIG. 8 a biosensing region 105 is present underneath the sacrificial layer 102.

According to an embodiment of the disclosure, the substrate 101 forms a wall of a micro-fluidic channel 106 and the sacrificial layer 102 is accessible to a fluid propagating through the micro-fluidic channel 106. According to an embodiment of the disclosure, a biosensing region may be present underneath the sacrificial layer 102.

Figure 9:
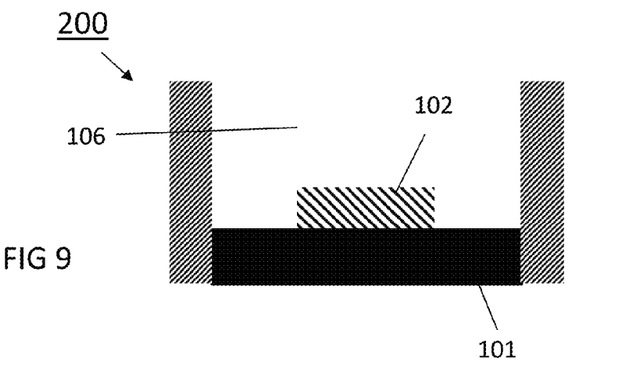
FIG. 9 illustrates an open micro-fluidic channel with a substrate and a sacrificial layer.

The intermediate device may comprise a micro-fluidic channel 106 in that the substrate functions as a wall of the micro-fluidic channel 106. As an advantage, when a fluid propagates through the micro-fluidic channel 106, the fluid is in direct contact with the substrate 101. The sacrificial layer 102 present on the substrate may be removed by flowing an etching product through the micro-fluidic channel 106. Such an embodiment is illustrated in FIG. 9. The micro-fluidic channel 106 may be fabricated from a single piece of silicon (e.g., etched in a single piece of silicon) wherein a sacrificial layer is deposited on one of the walls of the micro-fluidic channel, e.g., using a mask.

Figure 10:
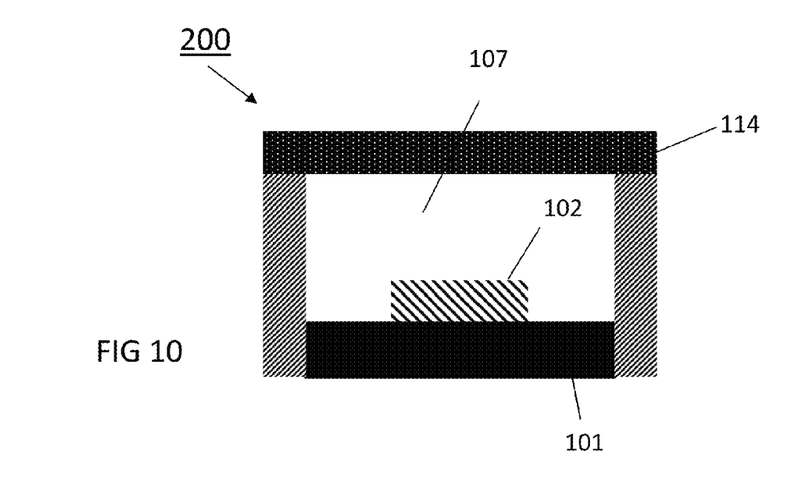
FIG. 10 illustrates a closed micro-fluidic channel with a substrate and a sacrificial layer.

According to an embodiment of the disclosure the micro-fluidic channel is a closed micro-fluidic channel 107. The use of a closed micro-fluidic channel 107 poses the problem of removing the sacrificial layer using specific dry etching masks. Further, high acidity etching products cannot be used as these may damage functional layer present in the closed micro-fluidic channel 107. The use of a material that may be removed with aqueous acidic etching products for the sacrificial layer provides a solution to this problem. The sacrificial layer may be removed by flowing an aqueous acidic etching product through the closed micro-fluidic channel 107. As an advantage, the technique can be used to create patterns in a closed micro-fluidic channel 107. Functional layers that may be present in the closed micro-fluidic channel 107 and any a biosensing region 105 present underneath the sacrificial layer remain intact due to the nature of the etching products. Such an embodiment is illustrated in FIG. 10. In the figure, the micro-fluidic channel 107 is closed with a lid 114.

The intermediate device may be fabricated by: 1) etching a micro-fluidic channel in a substrate and depositing a sacrificial layer on an inner wall of the micro-fluidic channel. Optionally, the micro-fluidic channel may be closed by placing a lid on the substrate. The closing may be done by bonding a lid, e.g. a glass lid, to the substrate using anodic bonding techniques. As discussed before, it is an advantage of the disclosure that the sacrificial layer is temperature resistant such that anodic bonding techniques can be used. This is illustrated in FIG. 10, wherein the lid 114 closes the micro-fluidic channel 107.

Figure 15A:
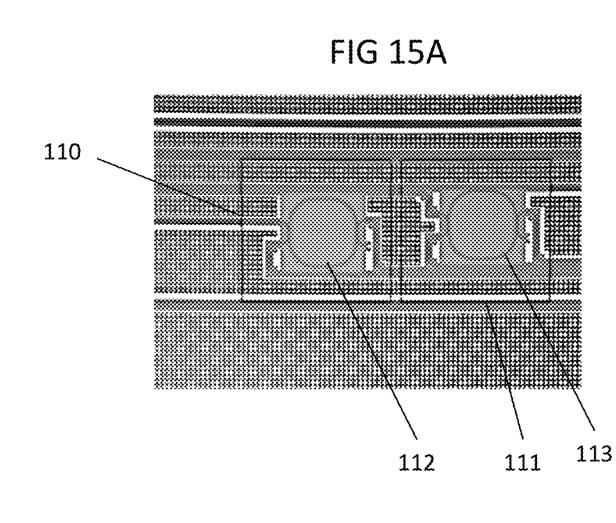
FIG. 15A is a bright-field microscopic image of two ring resonators structures, each covered with an AlOx sacrificial layer
Figure 15B:
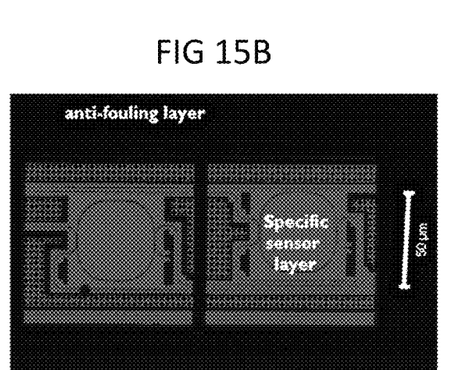
FIG. 15B is a fluorescent image of the ring resonator structures of FIG. 15A, after coupling of a DNA probe and binding of a fluorescent complement

The device as presented in the second aspect of the disclosure may be used in a biosensing system. This is illustrated in FIG. 15A and FIG. 15B. FIG. 15A is a bright-field microscopic image of an electronic circuit comprising two ring resonators structures (112, 113). Each ring resonators structure (112, 113) is covered with an AlOx sacrificial layer (110, 111). The AlOx layer is an $Al_2O_3$ layer with a thickness of 30 nm. Each sacrificial layer (110, 111) is a square which covers ring resonator structure (112, 113). Each ring resonator (112, 113) has a dimension of about 50 μm by 50 μm and is completely covered by a square of sacrificial layer material. Each square has a dimension of about 70 μm by 70 μm. FIG. 15B is a fluorescent image of the ring resonator structures (112, 113) of FIG. 15A, after coupling of a DNA probe and binding of a fluorescent complement. In the figure, two squares are illustrated. As can be seen, the complement only hybridizes to the lithographically pre-defined features. Hence, DNA probes only bind to the region that was previously covered by the sacrificial layer. In this embodiment, the sacrificial layers (AlOx layers) were deposited on the ring resonators using atomic layer deposition. In this embodiment, the first functional layer is an anti-fouling layer of PEO-silane. In this embodiment, the second functional layer is an azide silane. The DNA is coupled to the azide silane via click reaction. In this embodiment, alkyn-modified DNA probes were spotted using a non-contact dispensing tool. Thereafter, hybridization of fluorescent DNA complement is performed. After these steps, the fluorescent image FIG. 15B was obtained.

The following section describes experimental results.

a) Materials and Methods

Silicon Substrates

Preconditioning of Glass Containers

Prior to coating, the reaction chambers were first coated with the silane of interest. Hereto the glass containers were first cleaned with acetone and isopropyl alcohol. Afterwards, they were placed in an oven at 110° C. for 15 min to ensure that no water residues were left behind. After cooling to room temperature, under a constant flow of $N_2$, they were filled with a solution of a silane that contains poly-ethylene oxide units, i.e., 0.5% v/v PEO6/9 silane in dry toluene with the addition of 0.08% v/v HCl. After 3 hours of incubation, the samples were rinsed toughly with toluene, acetone and ethanol and placed in the oven at 110° C. until use.

PEO 6/9 Silane Deposition

The samples were first cleaned using 10 min sonication in acetone followed by 10 min sonication in isopropanol. After drying with a $N_2$ gun they were placed in an $UV/O_3$ chamber for 15 min to remove all organic contamination from the surface. Immediately after exposure the samples were immersed overnight in the PEO6/9 silane solution, i.e., 0.5% v/v PEO6/9 silane in dry toluene with the addition of 0.08% v/v HCl. After sinalization, the samples were rinsed toughly with toluene, acetone and ethanol. Next the samples were dried under a stream of $N_2$ and baked in an oven at 110° C. for 15 min to allow the silane cross-linking.

Etching 3 different solutions were applied to perform the etching of the Aluminum oxide patterns; A 30% v/v $H_2O_2$ (hydrogen peroxide) in distilled water; tetra methyl ammonium hydroxide (OPD) and a phosphoric acid mixture (PAM) of 73% $H_3PO_4$ (phosphoric acid), 21.4% $H_2O$, 3.1% $HNO_3$ (nitric acid) and 3.3% acetic acid.

Azide-Silane Deposition

The samples were incubated in a preconditioned glass container with a solution of 2% v/v azide-silane and 0.5% v/v N,N-Diisopropylethylamine (DIPEA) in dry toluene under controlled $N_2$ atmosphere in a glove box. After 24 hours incubation, the samples were again rinsed toughly with toluene, acetone and IPA and placed in an oven at 110° C. for 30 min to allow cross-linking of the azide-silane.

Biofunctionalization

The N3-SAM modified samples were incubated for 1 h in an humidity chamber with a solution of 33.3% of 50 μM hexynyl-DNA in DIW, 22.2% of Tris[(1-benzyl-1H-1,2,3-triazol-4-yl)methyl]amine (TBTA) 2 mM in DMSO, 22.2% of Tetrakis(acetonitrile)copper(I) hexafluorophosphate (TCH) 2 mM in Sodium L-ascorbate (SA), Dimethyl sulfoxide (DMSO) and 22.2% of SA 2.6 mM in DI water. After incubation, the samples were rinsed toughly with DMSO. DNA hybridization was performed by incubating the samples in a 500 nM Cy3-labeled complementary DNA strand in hybridization buffer (1M NaCl, 10 mM tris(hydroxymethyl) aminomethane, 2 mM EDTA, pH 7). After 1 h of incubation, the samples were rinsed with hybridization buffer and kept in hybridization buffer until further analysis.

Characterization Techniques

Contact angle (CA) measurements were performed on 1 μl sessile drops of ultrapure water. The reported CA values were averaged over at least five distinct spots on two separate samples. Grazing angle infrared spectroscopy (GA-FTIR) measurements were performed over a wavenumber range of $3000\ cm^{-1}$ to $1000\ cm^{-1}$. The spectra are the result of the Fourier-Transformation of 2048 interferometric scans obtained with a resolution of $1\ cm^{-1}$. Bright field images were taken with a microscope using a 20× objective, 3 ms image acquisition time, 3.42% source intensity. At least three regions of the $SiO_2$ background and four regions of the $Al_2O_3$ patterns were selected to evaluate the intensity. Intensity histograms of these regions were obtained. Fluorescent images were taken using a microscope. Following parameters were applied: 5× and 20× objective, 500 ms acquisition time, 57.67% source intensity and Cy3 filter. Further, quartz crystal microbalance (QCM) measurements were performed. All experiments were performed at 21±0.02° C. with each solution introduced into the system under gravity-driven flow. All measurements were performed in a stagnant environment, resulting in diffusion controlled binding events. Frequency and dissipation changes of all four resonances were recorded. For all QCM measurements, the normalized frequency responses ($\Delta f_n/n$) were found to be similar over all harmonics. For clarity reasons, only the frequency and dissipation responses for the 3rd harmonic will be discussed. The Sauerbrey equation was is used to calculate the measured frequency change ($\Delta f$) into the adsorbed mass per unit area ($\Delta m$)

$$\Delta m = -C\Delta f/n$$

b) Results and Discussion

Etch Effect on PEO6/9 SAM Modified $SiO_2$ Samples

In order to use the sacrificial etch procedure, a first requirement is that the PEO6/9 SAM functionalized $SiO_2$ sample is not affected by the etch procedure used. To verify this, contact angle measurements were performed on a PEO6/9 SAM functionalized sample after etching in different solution, i.e., PAM, OPD and $H_2O_2$. As can be observed in FIG. 11, it was noticed that that the integrity of the PEO6/9 SAM was not maintained after etching in a basic OPD (pH ~14) solution. The contact angle dropped drastically to 5° after 60 min of etching. It can be assumed that this result is related to the fact that basic solutions are known to attack silanol groups (Si—O—Si). As a consequence, silane molecules were quickly detached from the $SiO_2$ silicon substrate. In contrast, the contact angle stayed stable after etching with the acidic PAM solution (pH ~1) and the more oxidative $H_2O_2$ solution. The observed variations are limited and did not exceed 5° even after 60 minutes of etching. These limited changes are indicative for a non-damaged PEO6/9 SAM coating.

Figure 12:
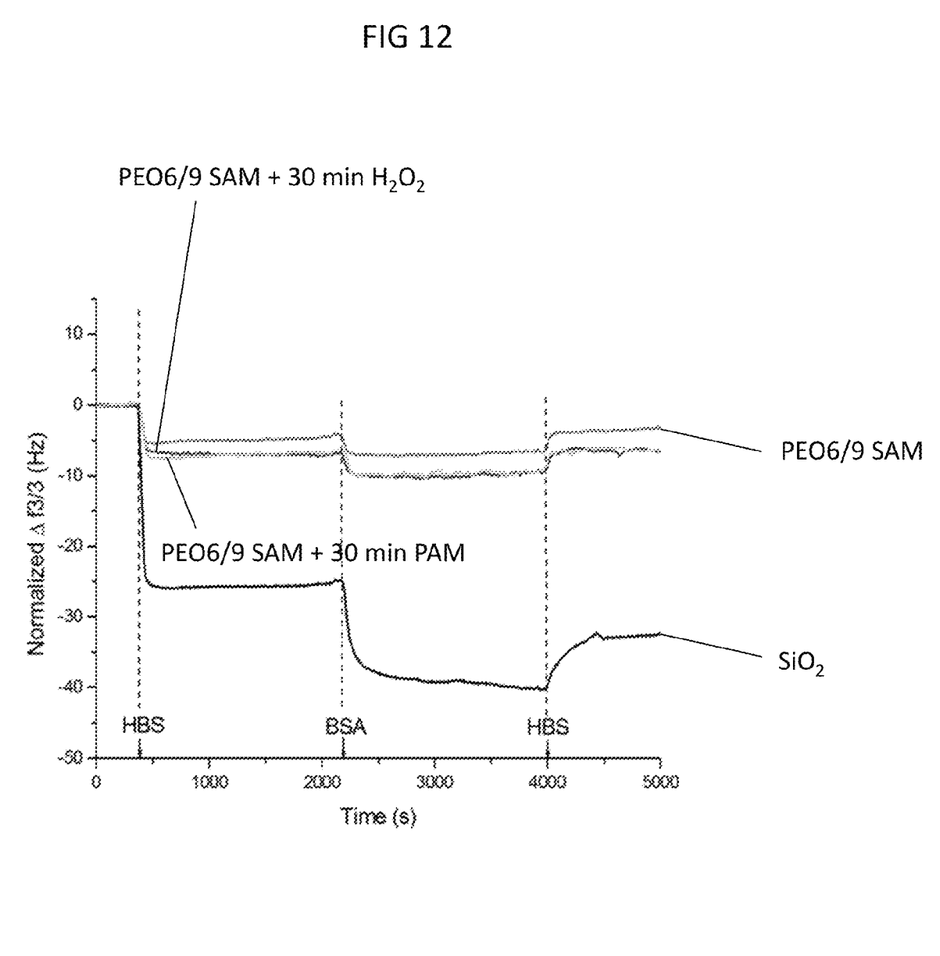
FIG. 12 illustrates the effect of a PAM etch on the protein resistant properties of the PEO6/9 SAM compared to a blank $SiO_2$ sample.

To gain more information on the anti-adhesive properties of the PEO6/9 SAM upon etching with either PAM or $H_2O_2$, protein adsorption measurements were performed using QCM. The results after etching with either PAM or $H_2O_2$ for 30 min are shown in FIG. 12. The black curve represents an untreated $SiO_2$ QCM crystal used as negative control and the middle grey curve represents the untreated PEO6/9 SAM-coated $SiO_2$ QCM crystal as the positive control. The light grey curve relates to 30 min treatment with PAM and the dark grey curve to 30 min treatment with $H_2O_2$.

The first negative frequency shifts observed in all graphs represents the switch from water to HBS buffer. This change from buffer is significant for the $SiO_2$ sample (−26 Hz) and limited for the treated and untreated PEO6/9 $SiO_2$ modified QCM-crystals (−6 Hz for untreated and ∼−8 Hz for 30 min exposure in ether PAM or $H_2O_2$). After 2000 seconds, a second negative frequency shifts is observed that resembles the arrival of bovine serum albumin (BSA) into the chamber. The negative control samples ($SiO_2$) showed a bigger frequency shift (−15 Hz) compared to the PEO6/9-SAM coated samples (−2 Hz). The curve observed on the latter $SiO_2$ sample is indicative for protein adsorption whereas no adsorption curve is observed on the PEO6/9 SAM coated samples. After BSA incubation for 30 min, positive shifts are observed due to the introduction of HBS buffer. All PEO6/9 SAM modified $SiO_2$ QCM crystals went back to their initial level before BSA arrival. This is a second indication that no proteins are left on the silicon substrate. Conversely, the negative control sample ($SiO_2$) did not reach his previous HBS level, indicative for protein adsorption. As compared to untreated PEO6/9 SAM, it is clear that the treatment either with PAM or $H_2O_2$ does not affect significantly the anti-adhesive properties of the PEO6/9 SAM.

From these results it was concluded that, even if structural or chemical changes could possibly occur due to PAM or $H_2O_2$ treatment, they are not causing degradation of the anti-adhesive properties of PEO.

Etching of the $Al_2O_3$ Patterns

Figure 13:
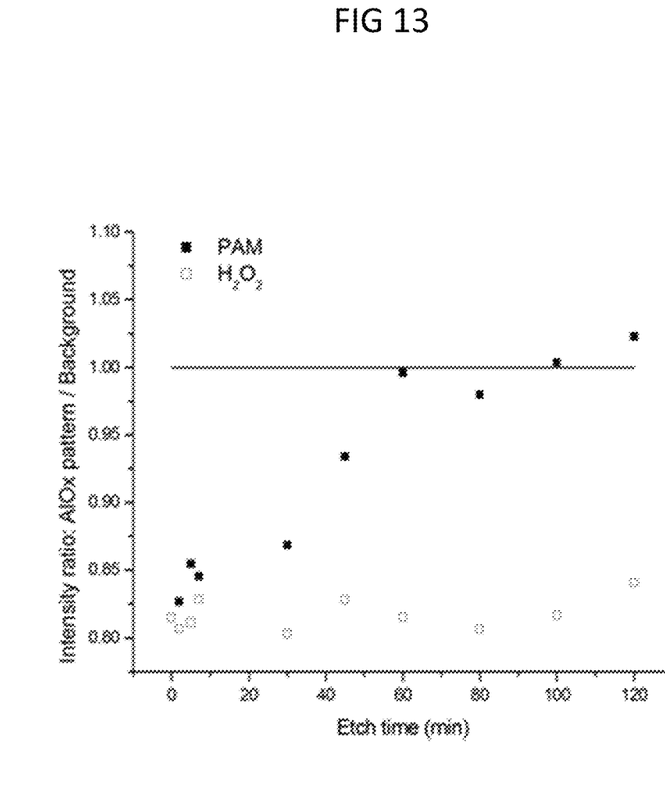
FIG. 13 illustrates the bright field intensity ratio of an Aluminum oxide pattern vs. the background signal after etching with PAM and $H_2O_2$.
Figure 14A:
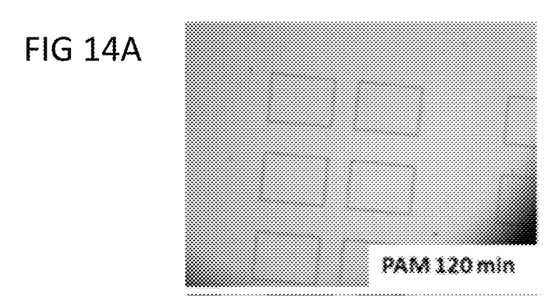
FIG. 14A illustrates a bright field image after 120 min etching in PAM.
Figure 14B:
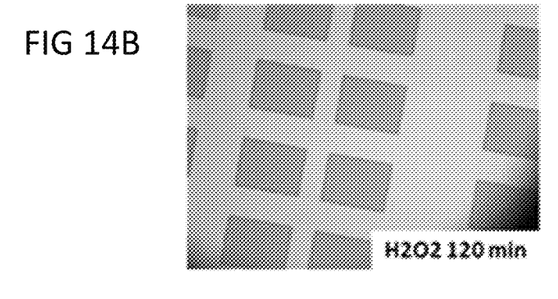
FIG. 14B illustrates a bright field image after 120 min etching in $H_2O_2$.

Results for the evaluation of $Al_2O_3$ oxide layer removal are represented in FIG. 13. This graph represents the ratio between the intensity measured in the patterned $Al_2O_3$ regions and the intensity of the $SiO_2$ background in function of etch time. Experimental data are marked by dots. Data for 0 min etching time represents the control sample, that is, intensity ratio for an untreated sample. As can be observed from this graph, the $H_2O_2$ treatment did not result in etched $Al_2O_3$ patterns as the patterns. FIG. 14B illustrates that after the 120 min $H_2O_2$ treatment the patterns are still clearly visible. In contrast, there are strong evidences that PAM removed the entire oxide layer after 60 min treatment since the intensity ratio progressively reached to unity for longer etching times. This is also illustrated in FIG. 14A.

Bio-Evaluation: Fluorescent Investigation of DNA Hybridization Assay

Fluorescent investigation: A) PEO6/9 SAM+Azide-SAM functionalized patterned sample before hybridization B) PEO6/9 SAM+Azide-SAM functionalized patterned sample after hybridization with the specific DNA complement C) PEO6/9 SAM+Azide-SAM functionalized patterned sample after hybridization with the non-specific DNA complement D) PEO6/9 SAM functionalized patterned sample after hybridization with the specific DNA complement. Fluorescent data are shown in FIG. 15. The fluorescent patterning investigation showed the desired results; the specific hybridization, i.e., hybridization with the specific complement yields a clear fluorescent pattern (FIG. 15 B). The etched areas are fluorescent and on top of the PEO-modified SiO2 areas, no fluorescence is observed. For the non-specific complement (FIG. 15C) no fluorescence is observed both on the patterns as on the PEO-modified SiO2 areas. Furthermore, on control samples (FIGS. 15 A and D), i.e., non etched sample, no fluorescence is observed.

CONCLUSION

It was shown that the anti-adhesive properties of PEO were maintained after long exposures to acidic and oxidative solutions but that basic solutions degraded strongly the PEO layers. In prior art techniques, an aluminum layer is used as a sacrificial layer to create patterns on a silicon substrate. To remove the aluminum layer, these basic solutions are used to etch the sacrificial layer. From the experiments, it is proven that the use of these basis solutions degrade functional layers that are present when etching the sacrificial layer.

Further, etch rates of these acidic and oxidative solutions were evaluated at room temperature on Al2O3 layers deposited by atomic layer deposition (ALD). It was shown that the etch rate of H2O2 was too slow to be retained and that the etch rate of PAM was 0.5 nm/min. Finally, spatial patterning was successfully achieved and evaluated via fluorescent antibodies and DNA.

We claim:

1. A method for creating a pattern on a substrate, the method comprising
   providing a substrate comprising silicon;
   creating a sacrificial layer on the substrate, wherein the sacrificial layer is formed on a first surface area of the substrate thereby leaving a second surface area exposed;
   depositing a first functional layer at least on the second surface area of the substrate;
   removing the sacrificial layer;
   wherein the substrate comprises a biosensing region underlying and in contact with the sacrificial layer and removing the sacrificial layer is performed by etching the sacrificial layer with an acidic solution that does not adversely affect the first functional layer and the substrate.

2. The method according to claim 1 wherein the acidic solution has a pH value between 0 and 8.

3. The method according to claim 1, wherein the sacrificial layer comprises a metal or a metal oxide.

4. The method according to claim 1, further comprising depositing a second functional layer on the substrate and wherein the second functional layer only binds to the first surface area of the substrate.

5. The method according to claim 1, wherein the acidic aqueous solution comprises phosphoric acid, nitric acid, sulfuric acid, hydrochloric acid or acetic acid or a combination thereof.

6. The method according to claim 1, wherein the substrate forms a wall of a micro-fluidic channel and wherein removing the sacrificial layer is performed by propagating an etching product through the micro-fluidic channel.

7. The method according to claim 6, wherein the micro-fluidic channel is closed along its length and open at each end.

8. The method according to claim 4, wherein the first functional layer is an antifouling coating and wherein the second functional layer is a functional coating, or wherein the first functional layer is a functional coating and wherein the second functional layer is an anti-fouling coating.

9. The method according to claim 4, wherein the first functional layer and/or the second functional layer comprises silane.

10. The method according to claim 2, wherein the sacrificial layer comprises a metal or a metal oxide.

11. The method according to claim 10, wherein the substrate forms a wall of a micro-fluidic channel and wherein removing the sacrificial layer is performed by propagating an etching product through the micro-fluidic channel.

12. The method according to claim 11, wherein the micro-fluidic channel is closed along its length and open at each end.

13. The method according to claim 3, wherein the metal oxide is aluminum oxide or germanium oxide.

* * * * *